United States Patent
Brinz et al.

(10) Patent No.: US 6,682,935 B2
(45) Date of Patent: Jan. 27, 2004

(54) OPTICAL SENSOR

(75) Inventors: Thomas Brinz, Bissingen Unter Der Teck (DE); Heidrun Potthast, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 294 days.

(21) Appl. No.: 09/894,781

(22) Filed: Jun. 28, 2001

(65) Prior Publication Data

US 2002/0028518 A1 Mar. 7, 2002

(30) Foreign Application Priority Data

Jun. 28, 2000 (DE) .......................................... 100 31 555

(51) Int. Cl.[7] .............................................. G01N 21/64
(52) U.S. Cl. ........................ 436/133; 436/134; 436/172; 422/56; 422/84; 422/91
(58) Field of Search .......................... 422/56, 57, 82.05, 422/82.08, 84, 85, 86, 91; 436/164, 133, 134, 172

(56) References Cited

U.S. PATENT DOCUMENTS

| | | | | | |
|---|---|---|---|---|---|
| 3,921,158 | A | * | 11/1975 | Anderson | 340/630 |
| 5,132,095 | A | * | 7/1992 | Koshiishi et al. | 422/82.07 |
| 5,173,432 | A | * | 12/1992 | Lefkowitz et al. | 436/138 |
| 5,244,810 | A | * | 9/1993 | Gottlieb | 436/68 |
| 5,470,755 | A | * | 11/1995 | Simon | 436/131 |
| 5,480,611 | A | | 1/1996 | Mills et al. | |
| 6,290,911 | B1 | * | 9/2001 | Lewis et al. | 422/82.02 |

* cited by examiner

Primary Examiner—Jeffrey Snay
(74) Attorney, Agent, or Firm—Kenyon & Kenyon

(57) ABSTRACT

An optical sensor is proposed for determining gases in gas mixtures, especially for determining one gas component in the air, having a sensitive layer exposed to the gas and having a device for detecting a change in an optical property of the sensitive layer. The sensitive layer of the sensor contains a phosphorus or nitrogen-containing base having numerous and/or long-chain alkyl groups for the pH adjustment of the sensitive layer.

20 Claims, 1 Drawing Sheet

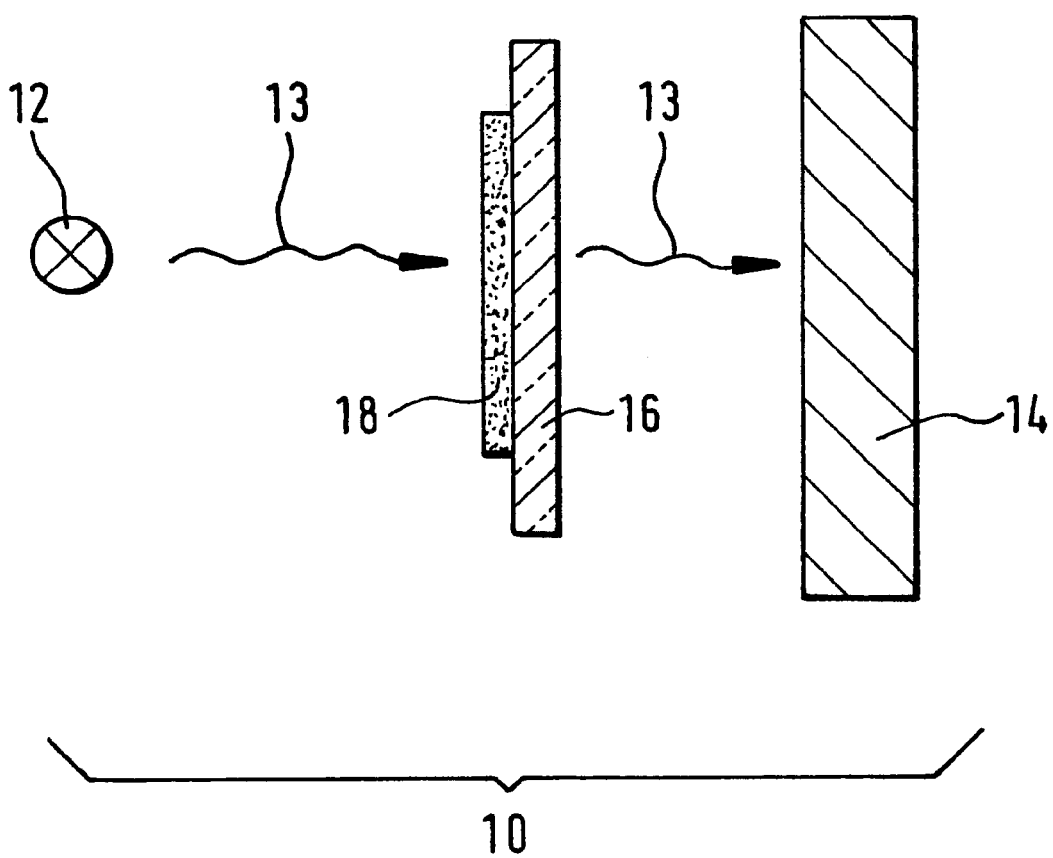

OPTICAL SENSOR

FIELD OF THE INVENTION

The present invention relates to an optical sensor.

BACKGROUND INFORMATION

Optical sensors for determining the concentration of a gas such as carbon dioxide in the air are used, among other things, in fire alarms. Their function is based on the fact that a sensitive layer of the sensor changes color reversibly upon contact with the gas to be determined. This change of color is recorded by a detector, and when a predetermined minimum concentration is exceeded, an alarm is triggered.

In U.S. Pat. No. 5,480,611 an optical sensor for determining carbon dioxide content of the air for medical applications is described, which has a layer sensitive to carbon dioxide applied to a substrate. This includes a fluorescing pH indicator, whose fluorescence changes as a function of the carbon dioxide concentration in the surrounding solution. In addition, the sensitive layer contains quaternary ammonium salts which provide for a basic environment in the sensitive layer and improve the $CO_2$ absorbing capacity of the layer. Tetraoctylammonium hydroxide is especially preferred for this purpose. However, during the production process of the sensor, this quaternary ammonium compound demonstrates poor miscibility with the polymer solution of which the sensitive layer is made.

SUMMARY OF THE INVENTION

It is an object of the present invention to produce an optical sensor for determining a gas which has a short response time and a high sensitivity, which is produced simply and therefore cost-effectively.

The optical sensor according to the present invention has the advantage that it has a very short response time and very high sensitivity with respect to a gas to be determined. This is achieved by adding to the sensitive layer of the sensor a phosphorus- or a nitrogen-containing base having numerous and/or long chain alkyl groups. Such bases demonstrate a sufficiently high basicity and very good miscibility with organic polymers. This simplifies the production of the sensitive layer of the sensor.

Thus, a phosphorus-containing base, preferably an alkylated phosphazene is used, because it most markedly shows the above-named favorable characteristics. Especially advantageous is the use of the phosphazene $P_4$-t-octyl, having the empirical formula $[(CH_3)_2N)_3P=N-]_3P=N(C_8H_{17})$.

According to the present invention, as a nitrogen-containing base, a quaternary ammonium salt is suitable, having long-chain alkyl groups which have more than 10 carbon atoms. In this regard, bases of the general composition $[(C_xH_{2x+1})_aNR_{4-a}]^+OH^-$ are especially advantageous, where R stands for an alkyl group, x is a number greater than 10 and a is a number between 1 and 4.

In addition, the sensitive layer of the sensor is advantageously made as a polymer matrix, and here the use of polydimethylsiloxane as the polymer leads to a great sensitivity of the layer on account of its characteristic gas permeability.

BRIEF DESCRIPTION OF THE DRAWING

The FIGURE shows a schematic representation of an exemplary embodiment of the optical sensor according to the present invention.

DETAILED DESCRIPTION

The optical sensor 10 illustrated in the Figure contains a radiation source 12 which may be such as a light-emitting diode, and a detector 14 which is developed, for example, as a photodiode. Between the radiation source 12 and the detector 14 a translucent substrate 16 made of glass is positioned. For the material of the translucent substrate 16, other optically transparent substances such as polymethacrylates can be used.

On the substrate 16 there is a sensitive layer 18, which reversibly changes its color when a minimum concentration of a gas to be determined is exceeded. The sensitive layer 18 includes a matrix in which there are the compounds responsible for the sensitivity of the sensor. In a preferred embodiment of the sensitive layer 18, this matrix is made of polydimethylsiloxane; but other silicones or polymers are also suitable, such as PVC and ethylcellulose.

For example, if polydimethylsiloxane is used as the matrix, sensitive layer 18 demonstrates a very good response to carbon dioxide, since the diffusion rate of $CO_2$ is very high on account of the good gas permeability of the polymer. The otherwise customary addition of plasticizers becomes unnecessary.

Alternatively, sensitive layer 18 can be applied directly to detector 14, while doing without substrate 16.

The functioning of sensitive layer 18 is based on its including a pH indicator and a base. The base effects a base environment in sensitive layer 18 and converts the pH indicator into its deprotonated form. As soon as an acid gas comes into contact with sensitive layer 18, it reacts with water contained in the layer and forms hydrogen carbonates $HCO_3^-$, as well as hydronium ions $H_3O^+$. This reaction changes the pH value of the layer and leads to a reprotonating of the pH indicator, whereby sensitive layer 18 changes color. The color transition is detected via an absorption or transmission measurement upon choice of the appropriate wavelength ranges of radiation (13) emitted by radiation source 12. Suitable pH indicators are such as cresol purple, thymol blue or brilliant yellow.

Tetraoctylammonium hydroxide is commonly applied as the base. However, using this base leads to problems in the production of sensitive layer 18.

During the production of the optical sensor, a solution is applied to substrate 16 which contains a polymer, a base and a pH indicator in a solvent, such as dichloromethane. During subsequent drying, sensitive layer 18 is produced as a thin film.

When tetraoctylammonium hydroxide is used as the base, the polymer solution demonstrates poor wetting of the substrate during application to substrate 16, and separation and the development of two phases can occur during the drying process.

If, on the other hand, a phosphorus- or nitrogen-containing base having numerous and/or long-chain alkyl groups is used, no wetting or separation problems at all show up during production of sensitive layer 18. In addition, these bases predominantly have a higher basicity than tetraoctylammonium hydroxide, and thus improve the response of the sensor.

As a phosphorus-containing base having numerous and/or long-chain alkyl groups, phosphazene $P_4$-t-octyl is especially suitable, and has the empirical formula $[((CH_3)_2N)_3P=N-]_3P=N(C_8H_{17})$ and the structural formula:

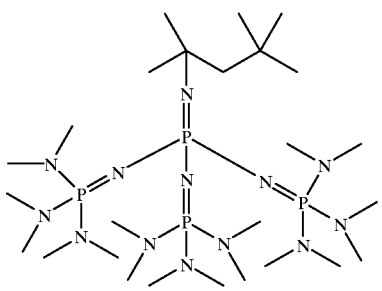

As nitrogen-containing bases having long-chain alkyl groups quaternary ammonium compounds are suitable, having the general composition $[(C_xH_{2x+1})_a NR_{4-a})]^+OH^-$, where R stands for an alkyl group, x is a number greater than 10 and a is a number between 1 and 4. As particularly suitable representatives of this class of compounds, $[(C_{12}H_{25})_3N(CH_3)]^+OH^-$ and $[(C_{18}H_{37})_4N]^+OH^-$ might be named.

The present invention is not limited to the exemplary embodiment described, but, besides the optical sensor for determining gases illustrated in the Figure and described, a series of further specific embodiments and applications are conceivable, in which a phosphorus- or nitrogen-containing base having numerous and/or long-chain alkyl groups as component of a sensitive layer for improving the sensitivity of a gas sensor. This applies in particular to tests for $CO_2$, but also to tests for $NO_x$, $SO_2$, $SO_3$ and/or halogen-hydrogen compounds.

What is claimed is:

1. An optical sensor for determining a gas in a gas mixture, comprising:
   a sensitive layer exposed to the gas; and
   an arrangement for detecting a change in an optical property of the sensitive layer; wherein:
   the sensitive layer includes a base that contains one of phosphorus and nitrogen and that includes at least one of numerous and long-chain alkyl groups, and
   the sensitive layer includes an alkylated phosphazene.

2. The optical sensor according to claim 1, wherein:
   the optical sensor is for determining a gas component in air.

3. The optical sensor according to claim 1, wherein:
   the alkylated phosphazene has the general formula $[(R^a_2N)_3P=N-]_3P=NR^b$, and
   $R^a$, $R^b$ each stand for alkyl groups.

4. The optical sensor according to claim 3, wherein:
   the alkylated phosphazene is $P_4$-t-octyl having the empirical formula $[((CH_3)_2N)_3P=N-]_3P=N(C_8H_{17})$.

5. The optical sensor according to claim 1, wherein:
   the alkylated phosphazene is contained as phosphazinium cation in the sensitive layer.

6. The optical sensor according to claim 5, wherein:
   the sensitive layer includes an alkylated phosphazinium hydroxide.

7. The optical sensor according to claim 1, further comprising: a substrate, wherein:
   the sensitive layer is positioned on at least one of the substrate and the arrangement for detecting.

8. The optical sensor according to claim 1, wherein:
   the arrangement for detecting includes a detector.

9. The optical sensor according to claim 1, wherein:
   the sensitive layer includes a polymer.

10. The optical sensor according to claim 9, wherein:
    the polymer is a gas-permeable polymer corresponding to polydimethylsiloxane.

11. A method of using an optical sensor for determining a gas in a gas mixture and including a sensitive layer exposed to the gas, and an arrangement for detecting a change in an optical property of the sensitive layer, the sensitive layer including a base that contains one of phosphorus and nitrogen and including at least one of numerous and long-chain alkyl groups, the method comprising the step of:
    operating the optical sensor as a sensitive element in a fire alarm;
    wherein the sensitive layer includes an alkylated phosphazene.

12. The method according to claim 11, wherein:
    the alkylated phosphazene has the general formula $[(R^a_2N)_3P=N-]_3P=NR^b$, and $R^a$, $R_b$ each stand for alkyl groups.

13. The method according to claim 12, wherein:
    the alkylated phosphazene is $P_4$-t-octyl having the empirical formula $[((CH_3)_2N)_3P=N-]_3P=N(C_8H_{17})$.

14. The method according to claim 11, wherein:
    the alkylated phosphazene is contained as phosphazinium cation in the sensitive layer.

15. The method according to claim 14, wherein:
    the sensitive layer includes an alkylated phosphazinium hydroxide.

16. A method of using an optical sensor for determining a gas in a gas mixture and including a sensitive layer exposed to the gas, and an arrangement for detecting a change in an optical property of the sensitive layer, the sensitive layer including a base that contains one of phosphorus and nitrogen and including at least one of numerous and long-chain alkyl groups, the method comprising the step of:
    operating the optical sensor as a sensitive element for determining at least one of $C0_2$, $NO_x$, $SO_2$, $SO_3$, and a halogen-hydrogen compound;
    wherein the sensitive layer includes an alkylated phosphazene.

17. The method according to claim 16, wherein:
    the alkylated phosphazene has the general formula $[(R^a_2N)_3P=N-]_3P=NR^b$, and
    $R^a$, $R^b$ each stand for alkyl groups.

18. The method according to claim 17, wherein:
    the alkylated phosphazene is $P_4$-t-octyl having the empirical formula $[((CH_3)_2N)_3P=N-]_3P=N(C_8H_{17})$.

19. The method according to claim 16, wherein:
    the alkylated phosphazene is contained as phosphazinium cation in the sensitive layer.

20. The method according to claim 19, wherein:
    the sensitive layer includes an alkylated phosphazinium hydroxide.

* * * * *